(12) United States Patent
Lerner

(10) Patent No.: US 7,033,598 B2
(45) Date of Patent: Apr. 25, 2006

(54) METHODS AND APPARATUS FOR ENHANCED AND CONTROLLED DELIVERY OF A BIOLOGICALLY ACTIVE AGENT INTO THE CENTRAL NERVOUS SYSTEM OF A MAMMAL

(75) Inventor: Eduard N. Lerner, Amsterdam (NL)

(73) Assignee: Intrabrain International N.V., Curacao (AN)

( * ) Notice: Subject to any disclaimer, the term of this patent is extended or adjusted under 35 U.S.C. 154(b) by 276 days.

(21) Appl. No.: 10/051,817

(22) Filed: Jan. 18, 2002

(65) Prior Publication Data

US 2002/0183683 A1 Dec. 5, 2002

Related U.S. Application Data

(63) Continuation-in-part of application No. 09/197,133, filed on Nov. 20, 1998, now Pat. No. 6,410,046, which is a continuation of application No. PCT/EP96/05086, filed on Nov. 19, 1995.

(51) Int. Cl.
*A61K 9/52* (2006.01)
*A61F 13/02* (2006.01)
*A61F 2/02* (2006.01)

(52) U.S. Cl. .................. 424/400; 424/434; 424/427; 424/428

(58) Field of Classification Search .............. 424/400, 424/434, 427, 428, 423, 449
See application file for complete search history.

(56) References Cited

U.S. PATENT DOCUMENTS

| | | | |
|---|---|---|---|
| 3,991,755 A | 11/1976 | Vernon et al. | |
| 4,250,878 A | 2/1981 | Jacobsen et al. | |
| 4,398,545 A | 8/1983 | Wilson | |
| 4,441,359 A | 4/1984 | Ezoe | |
| 4,564,016 A | 1/1986 | Maurice et al. | |
| 4,883,660 A | 11/1989 | Blackman et al. | |
| 5,087,243 A | 2/1992 | Avitall | |
| 5,169,384 A | 12/1992 | Bosniak et al. | |
| 5,222,936 A | 6/1993 | Stephen et al. | |
| 5,232,441 A | 8/1993 | Stephen et al. | |
| 5,298,017 A | 3/1994 | Theeuwes et al. | |
| 5,302,172 A | 4/1994 | Sage, Jr. et al. | |
| 5,401,239 A | 3/1995 | Stephen et al. | |
| 5,486,160 A | 1/1996 | Rossi et al. | |
| 5,545,617 A | 8/1996 | Dartt et al. | |
| 5,588,961 A | 12/1996 | Leone et al. | |
| 5,624,898 A | 4/1997 | Frey, II | |
| 5,720,720 A | 2/1998 | Laske et al. | |
| 5,728,068 A | 3/1998 | Leone et al. | |
| 5,807,306 A | 9/1998 | Shapland et al. | |
| 5,843,016 A | 12/1998 | Lugnani et al. | |
| 5,897,858 A | 4/1999 | Haslwanter et al. | |
| 5,993,435 A | 11/1999 | Haak et al. | |
| 6,001,088 A | 12/1999 | Roberts et al. | |
| 6,006,130 A | 12/1999 | Higo et al. | |
| 6,219,557 B1 | 4/2001 | Havinis | |
| 6,410,046 B1 * | 6/2002 | Lerner | 424/434 |

FOREIGN PATENT DOCUMENTS

| | | | |
|---|---|---|---|
| WO | WO97/18855 | * | 5/1997 |
| WO | WO 99/01229 | | 1/1999 |
| WO | WO 00/44350 | | 8/2000 |

* cited by examiner

*Primary Examiner*—Carlos A. Azpuru
(74) *Attorney, Agent, or Firm*—Nixon & Vanderhye P.C.

(57) ABSTRACT

Disclosed are invasive and non-invasive central nervous system (CNS) drug delivery methods and devices for use in these methods that essentially circumvent the blood-brain barrier. More specifically, the disclosed methods and devices utilize iontophoresis as delivery technique that allows for enhanced delivery of a biologically active agent into the CNS of a mammal as well as for (pre)-programmable and controlled transport.

31 Claims, 8 Drawing Sheets

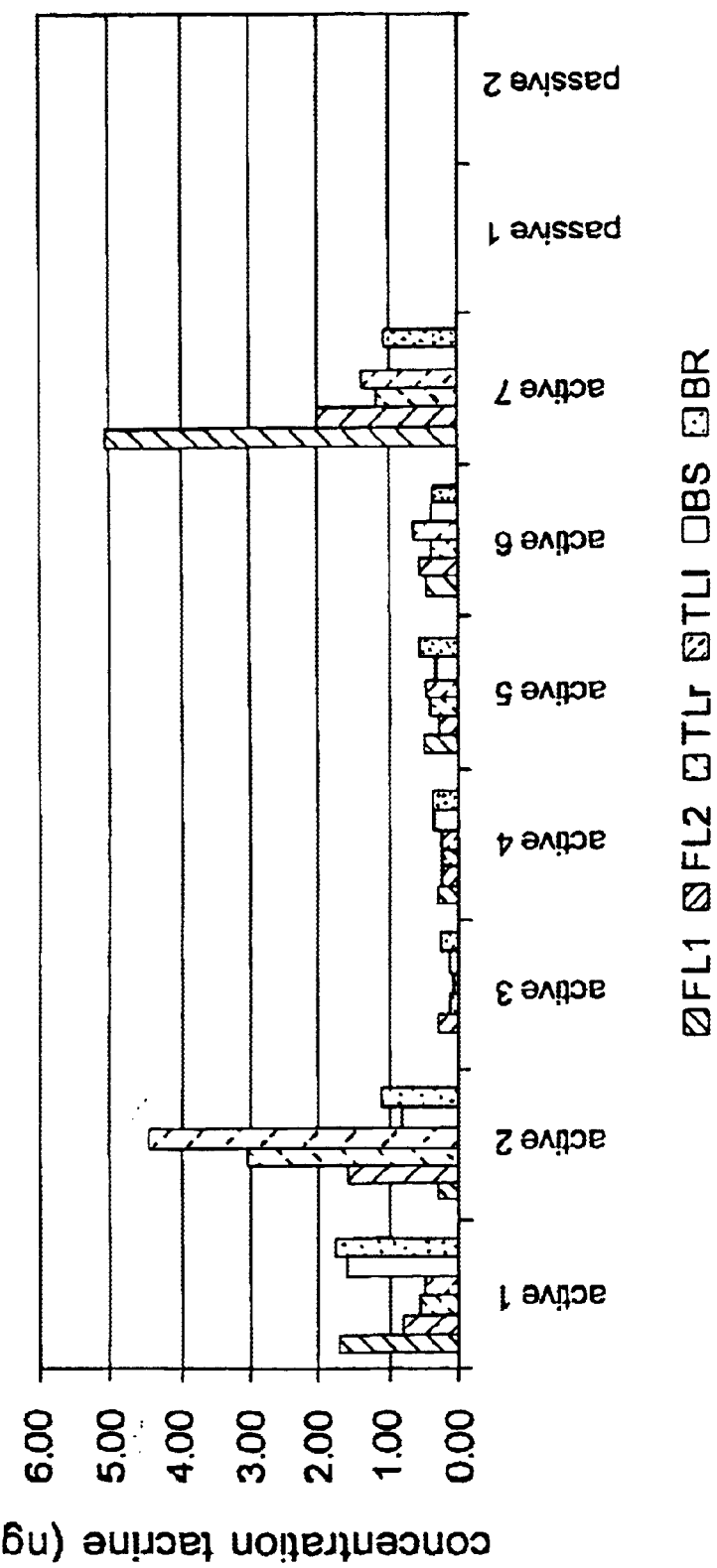

METHODS AND APPARATUS FOR ENHANCED AND CONTROLLED DELIVERY OF A BIOLOGICALLY ACTIVE AGENT INTO THE CENTRAL NERVOUS SYSTEM OF A MAMMAL

CROSS REFERENCE TO RELATED APPLICATIONS

This application is a continuation-in-part (CIP) of U.S. Ser. No. 09/197,133 filed Nov. 20, 1998 now U.S. Pat. No. 6,410,046, which is a continuation of PCT/EP96/05086 of Nov. 19, 1995 This is one of two sumultaneously filed CIPs of the '133 application.

FIELD OF THE INVENTION

The present invention relates to delivery methods and devices for effectively introducing a biologically active agent into deeper layers of the mammalian central nervous system (CNS). More specifically the invention relates to both invasive and non-invasive methods and devices for enhanced and controlled delivery of said agents into the mammalian CNS while circumventing the blood-brain barrier (BBB).

BACKGROUND OF THE INVENTION

A variety of approaches currently exist for delivering biologically active agents to the CNS. These include, among possible others, oral administration, intravenous—, intramuscular—and transcutaneous administration. All of the above drug delivery approaches tend to be systemic. Meaning that the drug is delivered into the systemic circulation, being carried to all internal organs and tissues and it has to pass through the blood-brain barrier (BBB) in order to access the CNS. Obviously, all other organs are being exposed to the drug, which may lead to a high incidence of side effects, particularly with those medications toxic to certain organs (e.g. nephrotoxic, hepatotoxic etc.). Most importantly, the therapeutic efficacy of numerous highly effective biologically active agents (e.g. large compounds, hydrophilic and charged substances such as peptides) is restricted, because they cannot or poorly penetrate the BBB, resulting in sub-therapeutic brain levels of these substances. High systemic levels have to be generated, in order to create therapeutic concentrations in the CNS, but for many therapeutic substances even this strategy is not always effective. Therefore, there is a large interest in development of alternative drug delivery methods for the central nervous system.

The above strategies are based on a pharmacological approach to solve the problem of BBB transport. Another strategy often employed in brain delivery is the use of invasive methods such as intraventricular infusion systems, intracerebral (polymeric) implants, transplantation of genetically engineered protein-secreting cells and cell implants. These methods are unfortunately only effective for drug delivery to the surface of the brain or to cells immediately adjacent to the depot or infusion site and can be used for example in the treatment of carcinomatous infiltration of the meninges. However, these methods have many limitations because effective drug concentrations in brain parenchyma cannot be achieved. There are two reasons for the poor drug distribution in the brain following local delivery from a depot or infusion site. At first the efficacy of diffusion decreases with the square of the distance and at second, molecules that are highly diffusible will be immediately transported out of the brain by means of transport across local capillaries.

Diffusion in the brain is slow and it has been reported that the time required to obtain 50% equilibration over distances of approximately 1 cm may take hours to days. Administration directly into the cerebrospinal fluid (CSF) will result in significant drug levels in only the outer few millimeters of the tissue adjacent to the ventricular and subarachnoid spaces. Another disadvantage of intraventricular infusion is the occurrence of drug distribution only to the ipsilateral brain, because of the unidirectional flow of CSF within the brain. Intraventricular administration can be compared with a slow, intravenous infusion causing the drug to be rapidly eliminated out of the brain, because the CSF volume in humans is completely recycled every four to five hours, the drug is thus readily distributed into the peripheral blood stream.

Drug distribution from the matrix of a polymeric implant or catheter of a CNS delivery device is based on passive diffusion, which is a slow process. During diffusion the drug may be subjected to substantial metabolism and clearance. As a result, the volume of tissue exposed to the drug is very small. The treatment volume of a polymeric implant or intraventricular infusion has been determined to be less than 1 mm and this is true for both small and large substances. The limited migration distance has been demonstrated with small molecules and with large molecules such as nerve growth factor (NGF). A consequence of the limited diffusion distance is that cells immediately adjacent to the intracerebral implant are being exposed to high and often toxic concentrations of the drug.

The maximal penetration of drug into brain parenchyma is <1 mm regardless of the mode of administration (intracerebral implant, microdialysis within the brain or intracerebroventricular infusion). This imposes a severe limitation in clinical situations where much larger treatment regions may be required.

Delivery through a chronically implanted canula in the CNS is described by Hargraves et al. and Yebenes et al. Harbaugh et al. described the use of implantable infusion pumps.

U.S. Pat. No. 5,720,720 discloses a convection-enhanced delivery catheter and method adapted to increase the migration distance of the infused drug by maintaining a pressure gradient during interstitial infusion. Two to ten-fold larger treatment volumes may be achieved following high-flow infusion for 12 hours using a microinfusion rate of 3 mu.l/min than can be achieved with low-flow infusion delivering the same mass using an infusion rate of 0.05 mu.l/min. Despite its large improvement in delivery efficiency this method has also some disadvantages such as the long infusion time, the risk of leakage of drug and the limited control of the distribution pattern within anisotropic media such as the white matter.

As with all catheter devices for intracerebral drug delivery, insertion of a device into a ventricle requires a risky surgical intervention that may cause serious tissue damage.

The present invention overcomes the disadvantages such as limited penetration depth of existing implantable delivery methods by using iontophoresis as a drug delivery enhancement technique. Iontophoresis has been defined as the active introduction of ionised molecules into tissues by means of an electric current. The technique has been used to enhance drug delivery into tissues underlying the donor electrode (e.g. skin) as well as to the general blood circulation, thus providing systemic delivery of a drug to the entire body. Iontophoresis devices require at least two electrodes, both being in electrical contact with some portion of a biological membrane surface of the body. One electrode commonly referred to as the "donor" or "active" electrode, is the electrode from which the biologically active substance, such as a drug or prodrug, is delivered into the body. Another electrode having an opposite polarity functions to complete the electric circuit between the body and the electrical power source. This electrode is commonly referred to as the "receptor" or "passive" electrode. During iontophoresis, an electrical potential is applied over the electrodes, in order to create an electrical current to pass through the drug solution and the adjacent tissue.

Iontophoretic drug administration into body cavities by means of a catheter type of electrode has been first disclosed about 95 years ago. The Russians were in this field very productive and during the 1970's and 1980's a considerable number of patents were issued (e.g. SU Nos 532,890; 843,999; 1,005796). Recently, patents have been issued that disclose the treatment of blood-vessel related disorders (e.g. restenosis), bladder, uterus, urethra and prostate disorders. U.S. Pat. Nos. 6,219,557; 5,588,961; 5,843016; 5,486,160; 5,222,936; 5,232,441; 5,401,239 and 5,728,068 disclose different types of iontophoresis catheters for insertion into hollow, tubular organs (bladder, urethra and prostate) or into blood vessels. An implantable system for myocardial iontophoretic delivery of drugs to the heart is disclosed in U.S. Pat. No. 5,087,243.

Reference may be made to U.S. Pat. No. 5,807,306, which describes an iontophoresis catheter device for delivering a drug contained in a polymer matrix into internal tissue. The disclosed catheter may thus be an ideal tool for selective and controlled delivery to any body passageway or hollow organ. Because the drug is contained in a polymeric matrix, the risk of leakage typically associated with catheter devices is practically negligible. However, the disclosed device is not adapted to be implanted in the brain and is not suitable for long-term treatment. Furthermore, the device requires manual operation and it requires serious surgical intervention for intracerebral installation of the catheter.

The parent U.S. patent application of this CIP, Ser. No. 09/197,133 relates to a non-invasive method and device for delivery of a biologically active agent that is transported by means of iontophoresis and/or phonophoresis directly to the CNS using the olfactory pathway to the brain and thereby circumventing the BBB. This method we have called transnasal iontophoretic delivery. The present invention describes besides the non-invasive also invasive methods and devices for enhanced and controlled delivery of a biologically active agent to the CNS that also circumvents the BBB.

In humans and primates, the olfactory epithelium or olfactory mucosa is located at the top of the nasal cavity between the central nasal septum and the lateral wall of each main nasal passage. This region of the nasal cavity, which is free of airflow, lies just under the cribriform plate of the ethmoid bone that separates the nasal and cranial cavities. In humans the olfactory epithelium covers an area in the nose of approximately 2 $cm^2$ to 10 $cm^2$. The total olfactory surface area varies with age and between individuals. The olfactory area can be reached through the naris following the nasal septum in a superior and posterior direction. The middle turbinate, which closely opposes the septum usually prevents access to this region, fortunately, this obstruction is not surmountable.

In the last decade a number of articles were published that describe the delivery of drugs into the brain by administering the drug in the olfactory area and also a small number of patents have been issued that describe the use of the olfactory pathways to the brain as possible alternative drug delivery methods. For example, U.S. Pat. No. 5,624,898 issued by Frey W. H.; WO 033813A1 issued by Frey W. H.; WO 09901229A1 issued by Gizurarson S. and WO 044350A1 issued by Cevc et al. These patents all relate to the passive delivery of substances to the brain using the olfactory pathways. The agent is administered in the olfactory region and transport of the agent is based on passive diffusion through the olfactory epithelium. However, compounds that are hydrophilic, charged and/or larger than 300 Dalton may be not delivered in therapeutic effective amounts by the methods described in the cited references. These compounds, but also all other compounds may be delivered more rapidly and more effectively by means of a physical enhancement technique such as electrotransport and/or phonophoresis (sonophoresis). The use of an enhancement technique such as electrotransport has the additional advantage that it can provide a dose- and rate-controlled delivery of the biologically active agent and the dose can be pre-programmed according to individual needs.

Literature provides examples of methods to treat the nasal (respiratory) mucosa by means of iontophoresis, electrophoresis, and phonophoresis for allergy, rhinitis, sinusitis etc., and there are also papers that describe the use of nasal iontophoresis for systemic drug delivery. Already in 1937 Bailey L. et al. described the use of intranasal zinc iontophoresis to treat hay fever. (Bailey L. D. and Shields C.; *Br. Med J.* 1, 808, 1937). Other examples of nasal iontophoresis can be found in literature as for instance in; Weir et al., J. Laryngol. Otol. 81 (10): 1143–1150 (1967), Dadiomova et al., Vestn. Dermatol. Venerol. 43(7):72–74 (1969), Dainiak et al., Vestn. Otorinolaringol. May–June; (3): 26–34 (1979); Sokolova et al., Vestn. Otorinolaringol. November––December; (6):57–60 (1979); Krotkova et al., Zh. Vopr. Neirokhir. Im. N. N. Burdenko May–June; (3): 44–47 (1980); Buzek et al., Cas. Lek. Cesk.; 120 (51): 1561–1565 (1981) and Gronfors et al., Med. Prog. Technol.; 17 (2): 119–128 (1991). Examples of nasal iontophoresis electrodes for systemic delivery or local delivery are described in the following patents: U.S. Pat. No. 5,298,017 issued by Theeuwes et al., SU-992075 issued by Kens et al. and U.S. Pat. No. 6,001,088 issued by Roberts et al. that describes a method for delivery of a biologically active agent to the eye following iontophoresis through the nasal epithelium.

Systemic nasal drug delivery implicates that drugs are delivered through the respiratory epithelium of the nasal cavity. In contrast to the olfactory mucosa, the respiratory epithelium is easy accessible by means of for example; nose drops, nasal sprays and a possible iontophoresis or phonophoresis probe. However, the major reason why respiratory epithelium is the target site of nasal drug administration is its rich underlying vascular network, especially in the Kiesselbach's area. These blood vessels can be accessed immediately following absorption and blood flow distributes the drug throughout the rest of the body. The present invention is based on enhanced delivery of a biologically active agent through the olfactory epithelium of the nasal cavity. Vascularization in the olfactory region is much less compared to the anterior part of the nasal cavity. The olfactory epithelium has distinct anatomic differences with the respiratory epithelium (Graziadei P. P. C. and Monti-Graziadei, 1985, *Ann.NYacad.Sci*, 457,127–145). The olfactory epithelium being a sensitive neuroepithelium with poor regeneration properties whereas the respiratory epithelium is an "ordinary" squamous mucosal epithelium with good regeneration properties and having mucocilliary clearance. Due to the differences between these two types of epithelium and especially to the delicate nature of olfactory neuroepithelium compared to the respiratory mucosa, nasal compositions for the respiratory nasal mucosa will not automatically be appropriate for the olfactory mucosa. Also, iontophoresis parameters (e.g. current strength, wave-form, frequency, duration) for enhanced olfactory drug delivery will differ from enhanced transport through respiratory nasal mucosa use of nasal iontophoresis according to the present invention requires specific physicotechnical properties of the nasal electrode(s) that differ from the nasal electrodes described for local and systemic delivery through the respiratory epithelium. For example, the electrode must have such a shape to allow it to be inserted into the olfactory region through the olfactory cleft and to make an intimate contact with the olfactory mucosa.

An alternate BBB circumventing pathway to the brain is provided by the optic nerve. The optic nerve, which is about 4 cm long, is directed backwards and medially through the posterior part of the orbital cavity. It then runs through the optic canal into cranial cavity and joins the optic chiasma. The optic nerve is enclosed in three sheaths, which are continuous with the membranes of the brain, and are prolonged as far as the back of the eyeball. Therefore, there is a direct connection between the optic nerve and the brain structures. Itaya and van Hoessen described transneuronal retrograde labeling of neurons in the stratum griseum superficiale of the superior colliculus following intra-ocular injection of wheat germ agglutinin-horseradish peroxidase. A study of the distribution of wheat germ agglutinin-horseradish peroxidase in the visual system following intra-ocular injections in the chick, rat and monkey confirmed early findings of transneural transport of this conjugate in vivo. It is therefore envisioned that a biologically active agent can be delivered direct to the CNS by a non-invasive delivery method and apparatus that utilises the ocular pathway that circumvents the BBB.

SUMMARY OF THE INVENTION

The present invention provides invasive and non-invasive methods and devices for enhanced and controlled delivery of a biologically active agent directly into the CNS, thereby circumventing essentially the blood-brain barrier. The invasive methods involve a surgical intervention that is limited to a minimum compared to existing methods, because the delivery system is installed at an extracerebral location i.e. for example in the cranium, the epidural, or subdural spaces, on the brain surface or intrabrain. The non-invasive methods and devices utilise the olfactory or ocular pathway to the CNS and thus circumvent the BBB. Both invasive and non-invasive methods allow for achievement of therapeutic brain levels of a biologically active agent while effectively reducing the application or infusion time of said agent compared to existing methods.

In view of the limitations of existing CNS delivery systems, it is an object of the present invention to provide a method and device for enhanced and controlled administration of a biologically active agent that allows for effective concentrations of said agent in deeper tissue layers of the CNS while essentially circumventing the systemic compartment and the blood-brain barrier.

It is an object of the present invention to provide a method and device for enhanced and controlled CNS administration of a biologically active agent that requires a minimum of surgical intervention and that allows for a high level of safety with a minimum of local side effects.

It is a further object of the invention to provide a device of such design and made of such materials, as well as such a method for administration of a biologically active agent into the CNS that promotes high patient compliance and acceptance.

It is yet another object of the invention to provide a method and device for controlled and enhanced delivery of a biologically active agent into the CNS that is regulated by a feedback signal.

It is a further object of the present invention to thus treat CNS disorders.

These and other objects are accomplished by providing drug delivery methods and devices that use iontophoresis for controlled and enhanced delivery of a biologically active agent into the CNS. Phonophoresis may be chosen as an alternate delivery technique for the non-invasive delivery methods and devices of the present invention.

For the purpose of this invention, "iontophoresis" is defined as any form of electrotransport of a substance through mammalian tissue induced or enhanced by the application of an electrical potential. Thus, the term "iontophoresis" as used herein includes without limitation previously defined terms such as iontophoresis, electrotransport, iontokinesis and electroosmosis, and the combination of thereof, which comprises the transport of a substance induced or enhanced by the application of an electric potential.

"Olfactory region" or "olfactory area" of the human nose for the purpose of the disclosed invention defines the area of nasal mucosa that covers the olfactory cleft, as well as the septal mucosa of the superior and middle turbinates in the posterior and middle thirds of the nose.

As used in conjunction with the disclosed invention, the term "biologically active agent" as defined herein, is an agent, or its pharmaceutically acceptable salt, or mixture of compounds, which has therapeutic, prophylactic, pharmacological, physiological or diagnostic effects on a mammal and may also include one compound or mixture of compounds that produce more than one of these effects. Suitable therapeutic, pharmacological, physiological and/or prophylactic biologically active agents can be selected from the following listed, and are given as examples and without limitation: amino acids, anabolics, analgesics and antagonists, anaesthetics, anti-adrenergic agents, anti-asthmatics, anti-atherosclerotics, antibacterials, anticholesterolics, anti-coagulants, antidepressants, antidotes, anti-emetics, anti-epileptic drugs, anti-fibrinolytics, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, appetite stimulants, bacterial vaccines, bioflavonoids, calcium channel blockers, capillary stabilizing agents, coagulants, corticosteroids, detoxifying agents for cytostatic treatment, diagnostic agents (like contrast media, radiopaque agents and radioisotopes), drugs for treatment of chronic alcoholism, electrolytes, enzymes, enzyme inhibitors, ferments, ferment inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and nootropics, osmotic diuretics, parasympatholytics, parasympathomimetics, peptides, proteins, psychostimulants, respiratory stimulants, sedatives, serum lipid reducing agents, smooth muscle relaxants, sympatholytics, sympathomimetics, vasodilators, vasoprotectives, vectors for gene therapy, viral vaccines, viruses, vitamins, oligonucleotides and derivatives, and any therapeutic agent capable of affecting the nervous system.

Examples of biologically active agents, which may be preferentially administered using either the invasive or non-invasive methods disclosed here for enhanced delivery directly into the CNS and thereby essentially avoiding the systemic circulation include those biologically active agents degraded in the gastrointestinal tract, metabolised in an internal organ or in the blood, rapidly excreted from the bloodstream (e.g. through kidney clearance), and those with limited penetration of the blood-brain barrier. Also, those agents with systemic side effects will benefit from direct administration in the CNS avoiding the blood stream. Further those biologically active agents that at least partly target the CNS although the underlying disease may have systemic clinical manifestations (e.g. alpha-2-agonists and hypertension). Also, those that target the neural components of the olfactory pathway (e.g. therapeutics that promote regeneration of the olfactory bulb) or those that target neural components of the ocular pathway. Iontophoresis and/or phonophoresis provide thus a means for active transport of a biologically active agent into and/or through the ocular pathway or into and/or through the nasal mucosa, and into the olfactory pathways, and/or into the CNS. Also, iontophoresis and/or phonophoresis provide an active transport means to rapidly and effectively transport a biologically active agent out of the delivery device to the olfactory area of nasal mucosa to be treated or into the underlying tissues.

Other objects, features and advantages will be apparent from the following detailed description of preferred embodiments taken in conjunction with the accompanying drawing in which:

BRIEF DESCRIPTION OF THE DRAWING

FIG. 5 is a graph displaying the brain levels of Tacrine following transnasal iontophoretic delivery in exsanguinated animals. The abbreviations in the legend represent the following brain parts: FL1=basal part of the frontal lobe; FL2=convexital part of the frontal lobe; TLr=temporal lobe right; TL1=temporal lobe left; BS=brain stem and BR=remaining brain tissue.

DETAILED DESCRIPTION OF PREFERRED EMBODIMENTS

Invasive Methods and Devices

With the foregoing and other objects in view there is provided, in accordance with the invention, a method and implantable device for enhanced and controlled delivery of a biologically active agent comprising a donor electrode having an electroconductive member and a drug-containing compartment that is in electric contact with the electroconductive member and said drug containing compartment having a membrane or drug transfer part through which drug transfer takes place. The device further comprises a receptor electrode having an electroconductive member and an electrolyte-containing compartment. The device according to the present invention further comprises a power control unit (PCU) having integrated a (pre)-programmable power source and a microprocessor system. Said power control unit being electrically connected to the donor and receptor electrodes. The microprocessor regulates and controls the output current for iontophoresis and thus also the dosage of the biologically active agent. The donor electrode of the implantable device as disclosed in the present invention has a drug-containing compartment, which releases the biologically active agent over an extended period of time while at the same time preserving the bioactivity and bioavailability of the biologically active agent A first preferred embodiment of the invention as well as alternative preferred embodiments is now described in detail with reference to the drawings.

The method of this embodiment of the present invention involves surgically exposing an insertion or placement site that is generally located on the brain or in close proximity of the brain as for example in the following non-limited locations: epidural, sub-dural or in the cranium, followed by installation of the delivery device at the placement site.

Figure 1A:
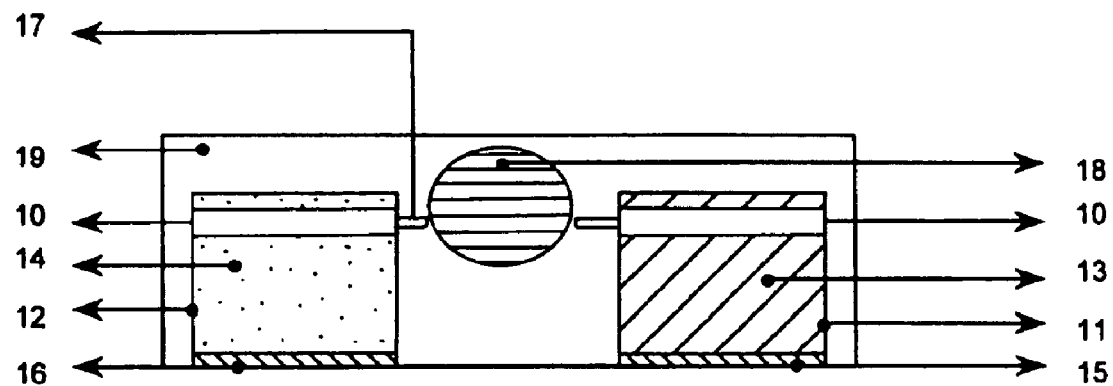
FIG. 1A is a schematic representation of the device according to a preferred embodiment of the present invention.

FIG. 1A shows a schematic representation of the delivery device. In this figure a device is shown that is especially suitable for superficially placement on for instance the brain surface or for subdural placement. The three basic components of the delivery device i.e. donor 12 and receptor 11 electrodes and the PCU 18 are contained in an insulating and non-degradable, biocompatible housing 19. The PCU is electrically connected to the electroconductive members 10 of both electrodes by internal connections 17. The drug-containing compartment contacts the underlying tissue by means of a drug-transfer part or membrane 16 that is preferably permeable for the biologically active agent to be delivered only upon current application. When there is no current applied the drug transfer part is preferably impermeable. Membrane 15 separates the electrolyte-containing compartment with the underlying tissue and preferably prevents in- or efflux of ions and other compounds when there is no current applied. Both membranes 15 and 16 are biocompatible and resistant to degradation. In this embodiment the device used in the method is installed as an integrated system.

The drug transfer part or membrane 16 as well as the electrolyte transfer part or membrane 15 may not necessarily being constructed from a material other than the drug reservoir or electrolyte reservoir but may be formed by a non-insulated part of the drug containing and/or electrolyte containing compartment respectively that is exposed to and in direct contact with the adjacent tissue.

Figure 1B:
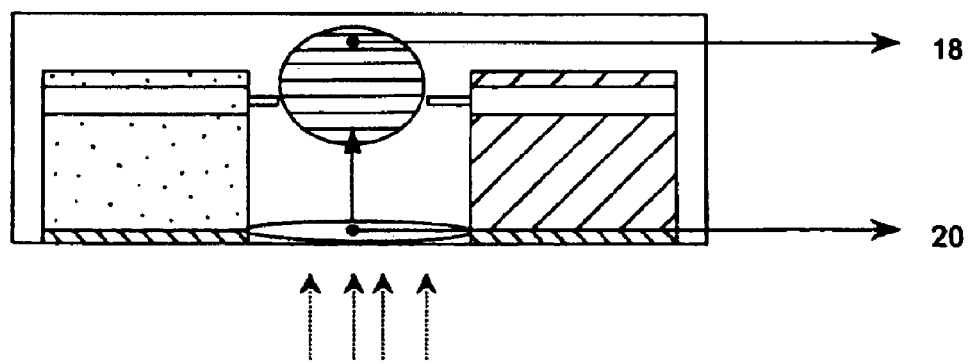
FIG. 1B is a schematic representation of the device according to another preferred embodiment of the present invention that comprises a biosensor that allows for feedback regulated delivery.
Figure 2A:
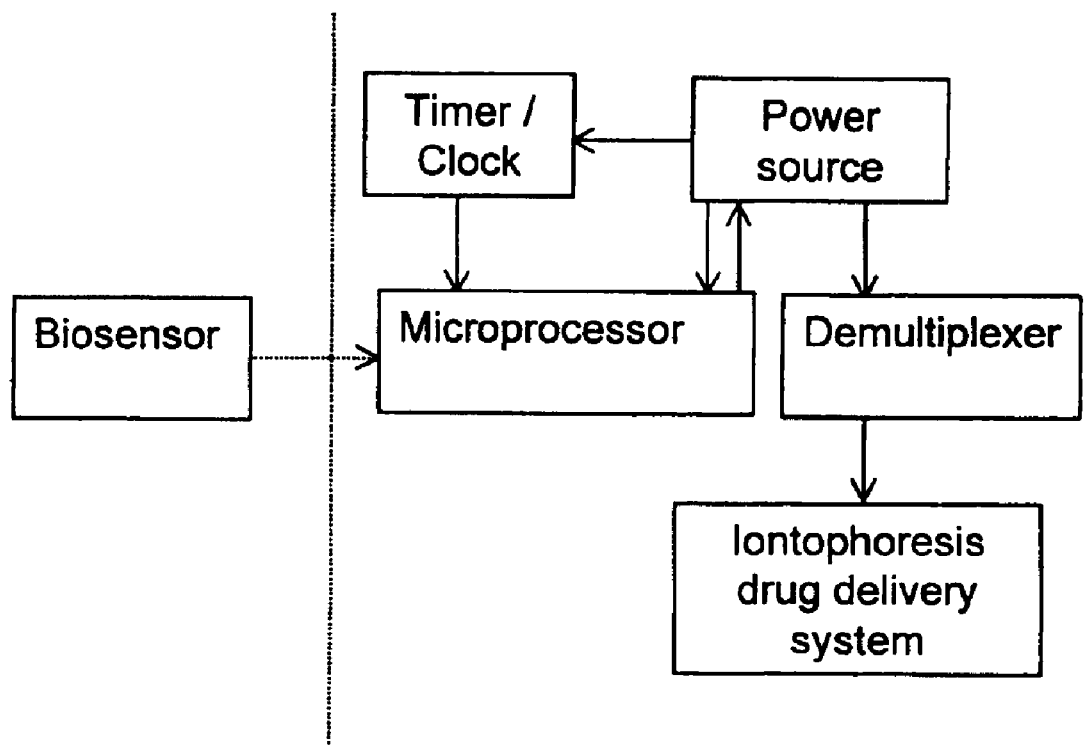
FIGS. 2A and B show a schematic overview of the PCU components
Figure 2B:
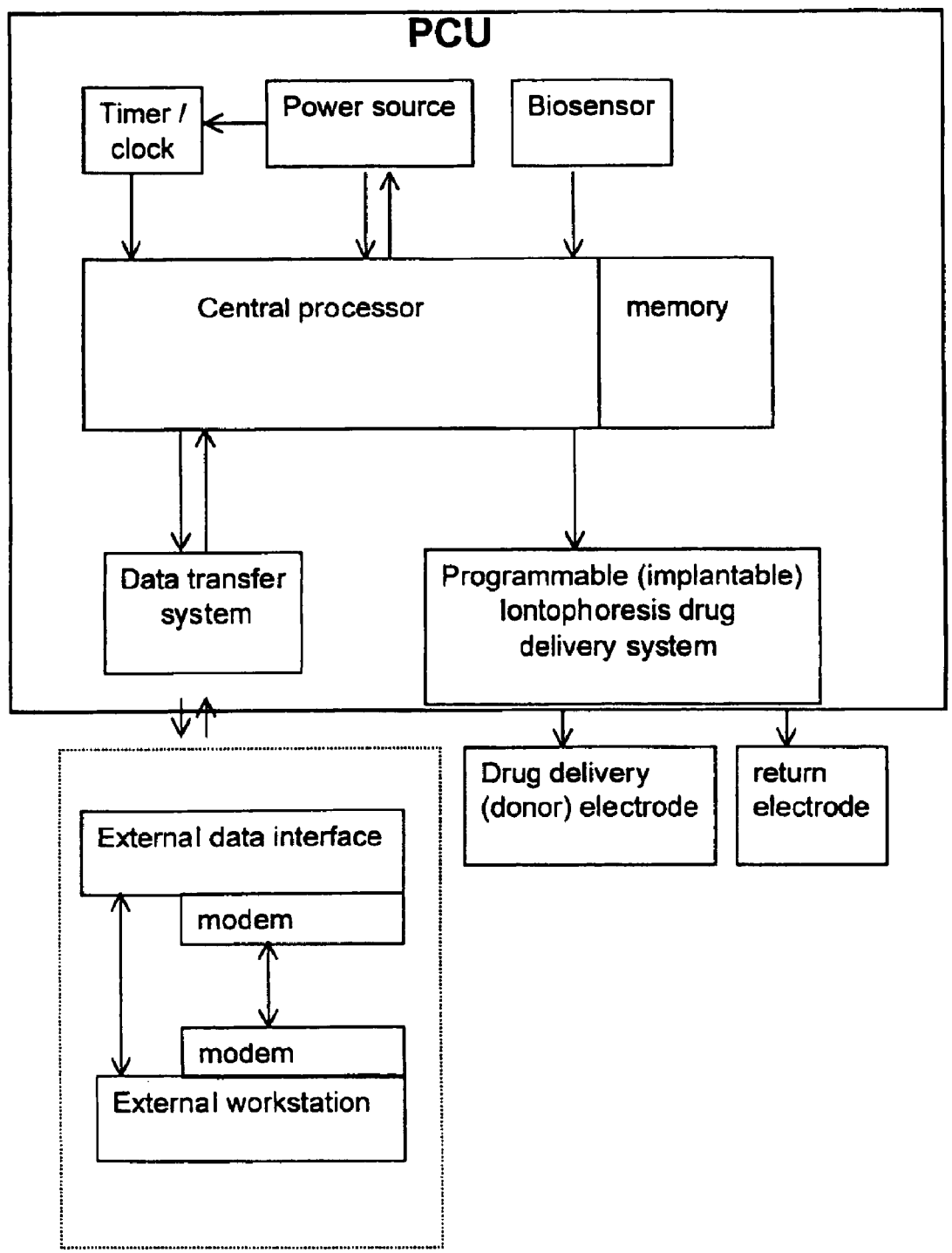

An alternative preferred embodiment of the device for use in the disclosed method is shown in FIG. 1B. The device comprises a biosensor 20 that is connected to the PCU. The biosensor may detect any physiological, physical or chemical signal upon which the PCU starts or stops a delivery program. In this way a feedback mechanism is provided that automatically controls the output current while for example monitoring the physiological condition of the treated subject. An example of the use of such a feedback mechanism is the early detection of an epileptic event by an abnormal signal pattern, upon detection of this signal a delivery program is started resulting in an enhanced delivery of an anti-epileptic agent from the donor electrode before the epileptic attack occurs. Normalization of the signal can be used as indicator for the PCU to stop the delivery program. The biosensor as used in the present invention may be selected from the type of sensors that are sensitive for the following non limiting signals known to those skilled in the art: physical (e.g. temperature, pressure, current strength, potentials as EEG, ECG etc.) or chemical (e.g. pH, electrochemical potential, concentration, etc.). Any appropriate sensor may be integrated in the delivery device according to the present invention and the type of sensor being dependent on the purpose of the delivery application.

Figure 3A:
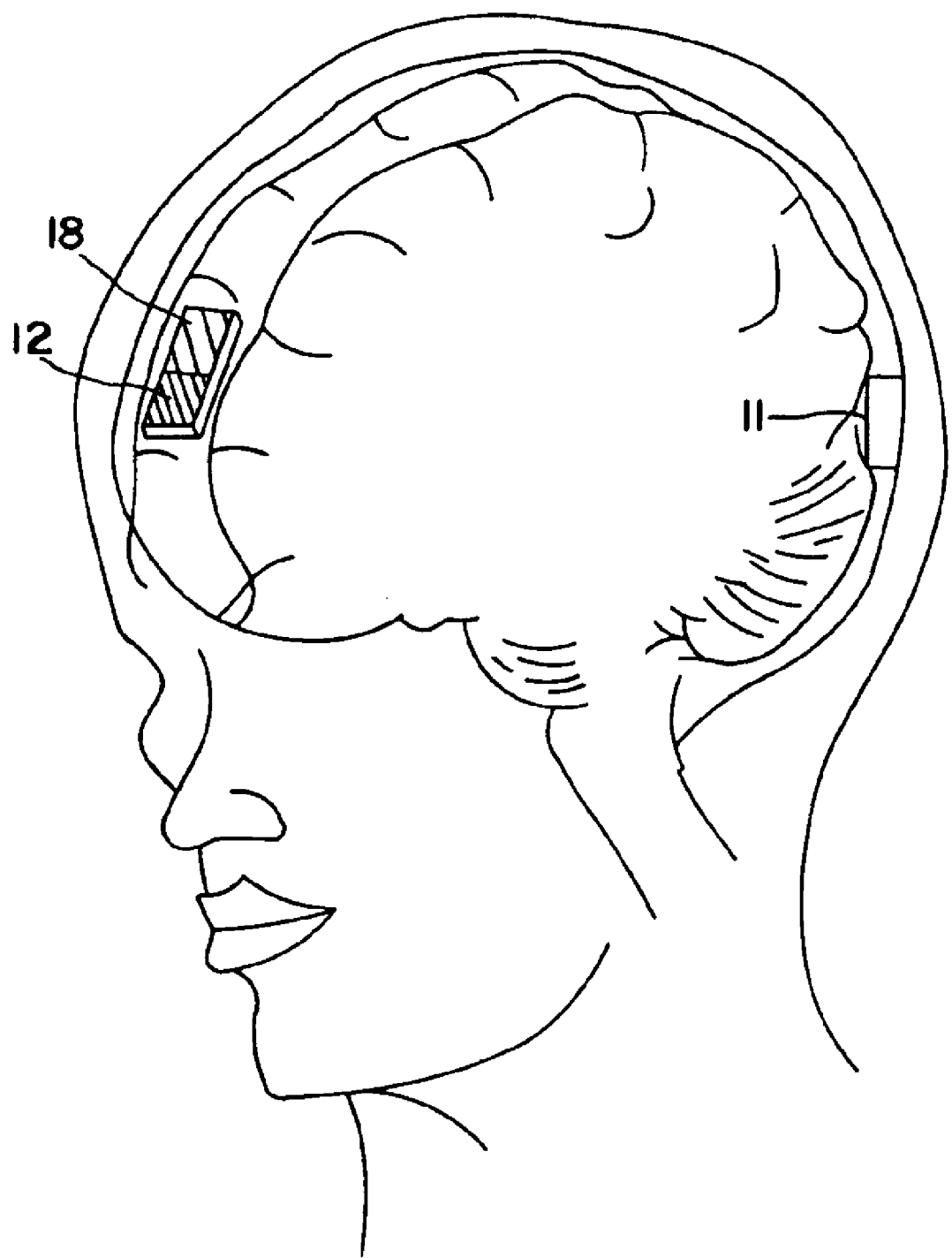
FIG. 3A shows the use of an implanted receptor electrode that is placed at a remote site from the donor electrode and the PCU.

In FIG. 3A another preferred embodiment of the invention is illustrated. Shown is a cross-sectional view of a human head that shows the use of implanted electrodes that are spaced apart and both electrodes are in contact with an underlying tissue. The receptor electrode is in electrical contact with the donor electrode and PCU unit.

Figure 3B:
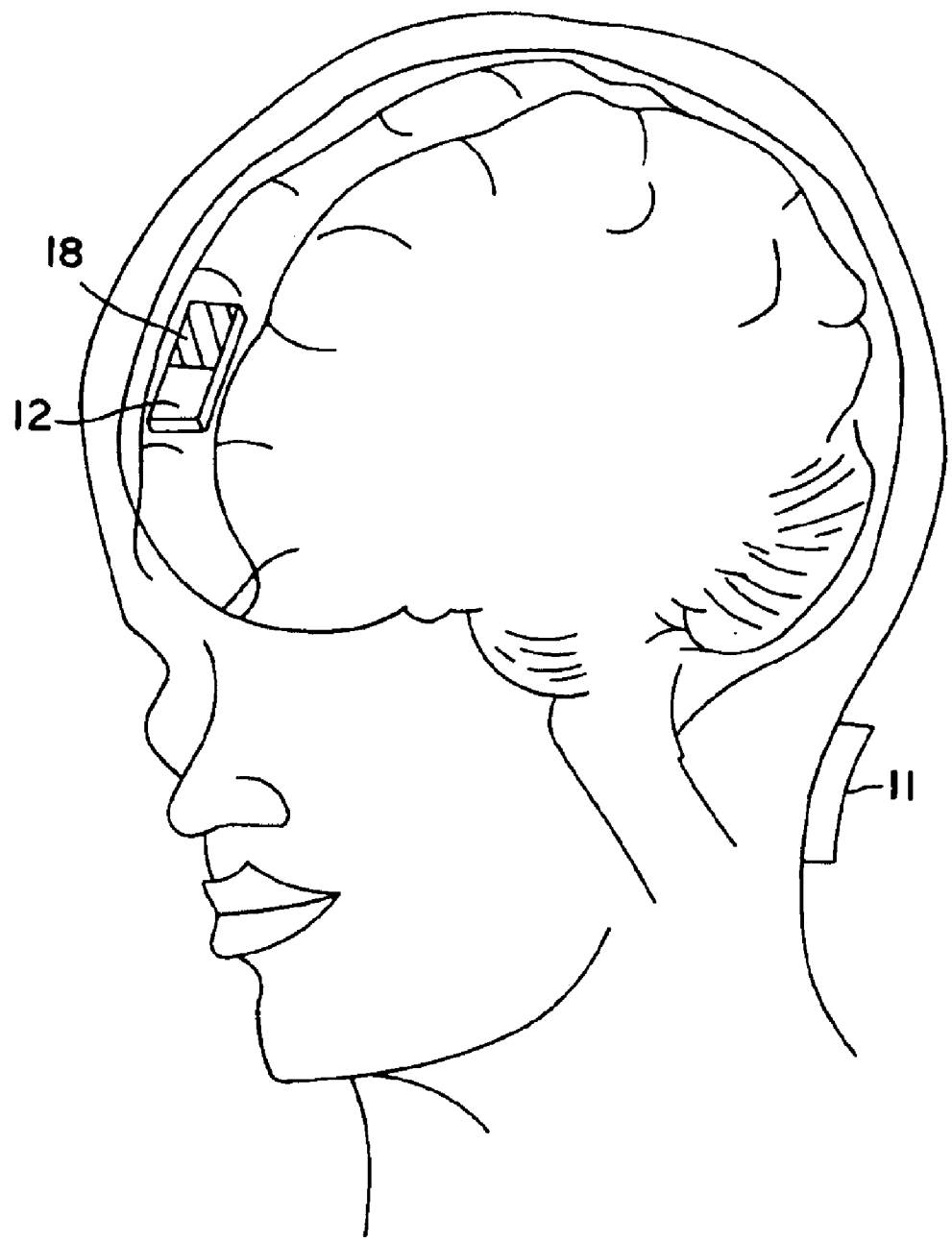
FIG. 3B shows the use of an externally positioned receptor electrode according to another embodiment.

FIG. 3B shows another preferred embodiment of the present invention wherein the receptor electrode is externally placed and most preferably at the back of the head, the mastoideus or neck.

Figure 3C:
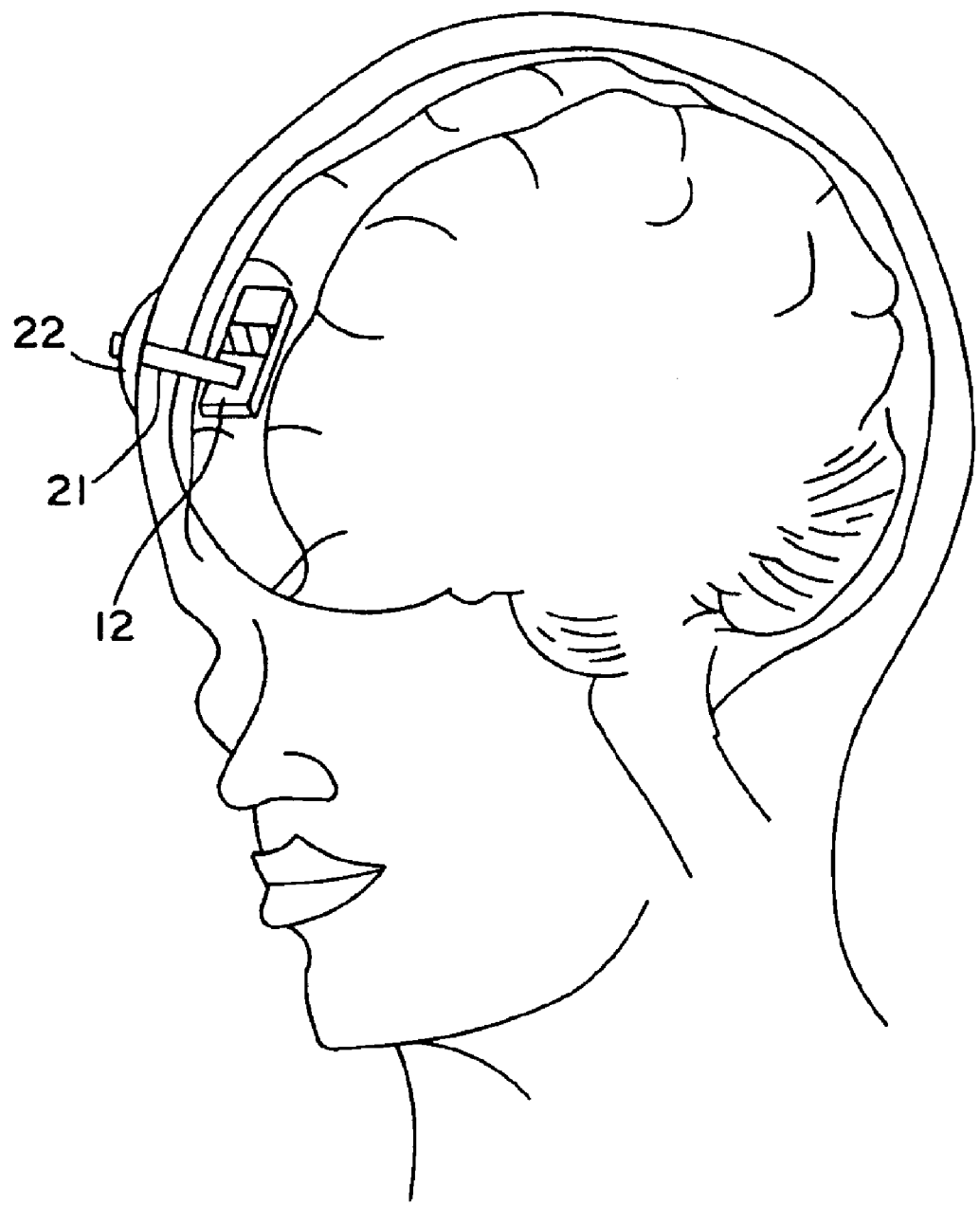
FIG. 3C is a schematic representation of yet another embodiment of the present invention that shows the use of refillable electrodes. Here is shown a refillable donor electrode.

FIG. 3C illustrates an optional and less preferred embodiment of the disclosed device that comprises an inlet for safe and accurate in situ refilling of the drug-containing compartment and/or the electrolyte-containing compartment. Here, a schematic refillable donor electrode is shown that comprises a tube 21 in contact with the drug-containing compartment that extends through the skull and skin and provides a sealed inlet port 22 for infusion of the biologically active agent. Mechanisms to prevent leakage, back flow of liquid into the filling tube and other problems associated with refillable implants may be used and are well known to those skilled in the art.

However, it is expected that the drug-containing compartment of the implanted delivery device having an appropriate size could release sufficient quantities of the biologically active agent for at least one year and possibly several years, because the absolute amounts of most biologically active agents required for brain delivery are very small.

In an alternative embodiment, the receptor electrode may comprise a plurality of implanted electrodes (more than one). In a yet other embodiment the receptor electrode may comprise a plurality of electrodes (more than one) with preferred site of positioning on the back of the head or neck. The positioning of the receptor electrode is crucial, because it has to create a vector of electrical field in such direction that it facilitates the drug transport into the CNS.

In a yet another alternate embodiment of the present invention the biologically active agent is enhanced and controlled delivered by means of administration to local spinal nervous tissue (spinal cord) and/or to the CNS. In this embodiment the donor electrode of the device being optimally adapted to be positioned to the spinal cord or in close vicinity of the spinal cord such as for example in the intrathecal, subdural or epidural space whereas the receptor electrode(s) may be implanted in a sub-cutaneous region of the abdomen or externally or any other body location in such a way that a vector is created that facilitates transport into the CNS or local spinal nervous tissue. The receptor electrode (s) in this spinal embodiment may alternatively being positioned externally of the mammal's body and most particularly a human being.

Expediently, the device according to the spinal embodiment the device is provided with a mean that allows for in situ refilling of the drug-containing compartment and/or electrolyte-containing compartment. Re-filling methods and devices are well known to those skilled in the art and mechanisms that prevent leakage, back flow of liquid into the filling tube and other problems associated with refillable implants may be used and are well known to those skilled in the art and are enclosed herein their entirety.

The electrodes 11 and 12 may be of reservoir-type or catheter-type or any other possible type of iontophoresis electrode known to those skilled in the art and may comprise for example a static implantable probe, a microdialysis probe or any other shaped implantable electrode known to those skilled in the art. Most importantly, the electrodes 11 and 12 being optimally adapted to be used in the present invention and have such a design, shape, size or material that it can be used in this invention.

The current strength delivered to the donor and receptor electrodes ranges between 0.001 to 10 $mA/cm^2$, and is preferably selected from the following range of 0.01 to 1.0 $mA/cm^2$. The PCU can be programmed to deliver any type of current waveform as for example, direct current or alternating current and the current may have any frequency, which depends on the compound to be delivered and the treatment requiring delivery of said compound.

In a preferred embodiment of the present invention the PCU can be externally programmed in order to adjust the delivery dose of the biologically active agent by a physician. Optionally, the delivery device may comprise means for telemetry that allows the physician to receive operational information of the device from a remote site.

With respect to the electroconductive members of the electrodes, which can be used in the present invention, they are comprised of electrically conductive material such as a metal like aluminium, stainless steel, gold, silver, titanium, and zinc. Examples of other suitable electrically conductive materials include but are not limited to: carbon, graphite, and metal salts like silver chloride. Electrodes may be formed of metal foil, metal screen, metal deposited or painted on a suitable carrier backing by means of calendaring, film evaporation, or by mixing the electrically conductive material in a polymer binder matrix. Alternatively, electrodes may be formed of a polymer matrix containing conductive filler material such as a metal powder, powdered graphite, carbon fibers, or other known electrically conductive filler material. Polymer based electrodes may be manufactured by mixing the conductive filler in a polymer matrix, preferably a mixture of hydrophilic and hydrophobic polymers. The hydrophobic polymers provide structural integrity, while the hydrophilic polymers may enhance ion transport. For example, metal powder, carbon powdered, carbon fibers and mixtures thereof can be mixed in a hydrophobic polymer matrix.

The donor and receptor electrode can be made of any suitable material or combination of materials, that fulfils relevant criteria with respect to compatibility with the biologically active agent in case of a donor electrode and with the biological environment, but also with respect to ease of manufacturing, sterilizability, re-usability, low environmental impact, flexibility, connectibility, disposability and durability. Furthermore, in case of a reservoir-type electrode, the reservoir should be constructed of any material in such way that it is adapted to absorb and hold a sufficient quantity of liquid in order to permit transport of the biologically active agent or electrolyte through its wall by means of iontophoresis. For example sponges, gauzes or pads consisting of cotton or other absorbent fabric, either or natural or synthetic origin, may be used.

More preferably, reservoirs are composed, at least in part, of one or more hydrophilic polymers. Typical preference is for hydrophilic polymers because water is the preferred ion transport medium and hydrophilic polymers have relatively high equilibrium water content. Multilayered solid polymer reservoir matrices are composed, at least in part of hydrophilic polymer. The form of the reservoir may be such as to enable its combination and attachment or coupling with the electroconductive member 10. The form, size and shape of the donor and/or receptor electrodes and their reservoirs are determined by the physiological, anatomical environment related to the application site.

The power supply used in conjunction with the present invention can be any small-size and lightweight cell. For example, the cells include manganese cells, alkali cells, lithium cells, unicad cells, silver oxide cells, mercury cells, air cells, alkali-manganese cells and plastic cells. Plastic cells are formed into button shape or sheet.

Non-Invasive Methods and Devices

The present invention is further directed to a method and apparatus for delivery of an effective amount of a biologically active agent directly into the central nervous system of a mammal, particularly a human being, that is in need of such a delivery with such an agent, wherein the delivery of said agent is enhanced by being made via the olfactory region in the nasal cavity or from the eyes of said mammal by means of energy-stimulated penetration generated and maintained by an applied energy field.

A method of treating diseases of the CNS and/or of the olfactory pathways comprises delivering a biologically active agent for enhanced transnasal delivery into the olfactory neural pathway and/or into the CNS thereby avoiding the systemic compartment comprises bringing the nasal mucosa in the olfactory area into contact with a delivery system. A second application of the disclosed transnasal drug delivery system is to treat the diseases of the olfactory system by enhancing the delivery of biologically active agents including those that facilitate regeneration of the neurons involved in the olfactory pathway. This approach allows both the delivery of a biologically active agent locally within the olfactory pathway(s) and the generation of high concentrations locally.

The method disclosed in the present invention in this preferred embodiment uses a transnasal delivery device, which is inserted in duplicate simultaneously in both nasal passages. In another embodiment, the device is inserted only in one nostril at a time, which improves the mammal's breathing function and increases the level of comfort. In the latter case, the device may be alternatively inserted into either nostril, or always in the same nostril that for some reason is preferred (better anatomical access to the olfactory region e.g. due to a deviated septum).

The preferred physical enhancement means is iontophoresis, which facilitates both transport of the biologically active agent out of the delivery device and/or through the olfactory mucosa, including olfactory nerve endings, cribriform lamina and other tissues in the olfactory region and possibly along the olfactory pathways. Another preferred transport means is phonophoresis. In a yet other preferred embodiment the transport means is iontophoresis in combination with phonophoresis.

In the present invention, the donor electrode (the biologically active agent travels away from it out of the device and into the nasal mucosa) is placed in the nasal cavity and most preferably in the olfactory region of the nasal cavity and comprises at least one or more electrodes which are located inside of the delivery device or directly connected to it (e.g. by a salt bridge). The receptor electrode (the biologically active agent travels towards it) is preferably located on a remote site outside the nasal cavity on the mammal's skin or mucous membrane.

In another preferred embodiment, the receptor electrode is positioned at the back of the mammal's head, at the mastoideus or in the neck. In an alternative embodiment, the receptor electrode may also be positioned inside the nasal cavity and may or may not be directly attached or connected to the body of the device. The receptor electrode may comprise a plurality of electrodes (more than one) with preferred site of positioning on the skin of the outside surface of the nose, or anywhere on the head or face. The positioning of the receptor electrode is crucial, because it has to create a vector of electrical field in such direction that it facilitates the drug transport into the CNS. The donor electrode utilized in the method of the present invention may be a reservoir-type or catheter-type or any other possible type of iontophoresis electrode known to those skilled in the art and that has such a design, shape, size or material that it can be used in this embodiment, but the most important feature is that the electrode fits comfortably into the nasal cavity of a mammal, more particularly a human being, and provides an intimate contact with the nasal mucosa in the olfactory area.

Importantly, the specific embodiment of the iontophoresis electrode or an ultrasound probe is crucial in the disclosed invention. It should have such shape so it can be inserted deep into the nasal cavity to the posterior third where the olfactory area is located in humans and primates. The electrode should have such a shape to conform to the nasal cavity in the olfactory region and to provide an adequate contact with the nasal mucosa in the olfactory area including the cribriform plate, as well as an acceptable level of comfort for the subject. Although the superior turbinate may also be used, the cribriform plate should be preferably avoided.

The receptor electrode will most commonly be in the form of an electroconductive pad, which contains an appropriate electrolyte composition (e.g. sodium chloride, phosphate-buffered saline) and which may be provided with an electroconductive adhesive layer for fixation to the skin.

With respect to the electrodes, which can be used in the present invention, they are comprised of electrically conductive material such as a metal like aluminium, stainless steel, gold, silver, titanium, and zinc. Examples of other suitable electrically conductive materials include but are not limited to: carbon, graphite, and metal salts like silver chloride. Electrodes may be formed of metal foil, metal screen, metal deposited or painted on a suitable carrier backing by means of calendaring, film evaporation or by mixing the electrically conductive material in a polymer binder matrix. Alternatively, electrodes may be formed of a polymer matrix containing conductive filler such as a metal powder, powdered graphite, carbon fibers, or other known electrically conductive filler material. Polymer based electrodes may be manufactured by mixing the conductive filler in a polymer matrix, preferably a mixture of hydrophilic and hydrophobic polymers. The hydrophobic polymers provide structural integrity, while the hydrophilic polymers may enhance ion transport. For example, metal powder, carbon powdered, carbon fibers and mixtures thereof can be mixed in a hydrophobic polymer matrix.

The electrodes can be made of any suitable material or combination of materials, that fulfils relevant criteria with respect to compatibility with the biologically active agent and with the biological environment, but also with respect to ease of manufacturing, sterilizability, re-usability, low environmental impact, flexibility, connectibility, disposability and durability. Furthermore, in case of a reservoir-type electrode, the reservoir containing the biologically active agent should be constructed of any material in such way that it is adapted to absorb and hold a sufficient quantity of liquid in order to permit transport of the active agent through its wall by means of iontophoresis. Optionally, the donor electrode reservoir should hold a self-sealing membrane or valve that allows the in-situ refilling with donor formulation, without the necessity of removal and re-insertion of the present device. For example sponges, gauzes or pads consisting of cotton or other absorbent fabric, either or natural or synthetic origin, may be used. More preferably, reservoirs are composed, at least in part, of one or more hydrophilic polymers. Typical preference is for hydrophilic polymers as for instance a hydrogel, because water is the preferred ion transport medium and hydrophilic polymers have relatively high equilibrium water content. Multilayered solid polymer reservoir matrices are composed, at least in part of hydrophilic polymer. The form of the reservoir may be such as to enable its combination and attachment or coupling with the donor electrode. The form, size and shape of the donor electrode and its drug-containing compartment are determined by the physiological, anatomical environment related to its application site, for instance in the nostril.

Instead of the polymer matrix, any material can be used, but preferably that with good elastic properties so that it can assume the shape of the nasal cavity in the olfactory region in order to provide an intimate contact between the drug transfer surface and the nasal mucosa and improve the subject's comfort. Any design, size or material of the donor electrode known to those skilled in the art can be used in this embodiment but the important feature is that the device fits comfortably into the nasal cavity of the subject and provides an intimate contact with the nasal mucosa in the olfactory area. The energy source connected with the electrodes of the present device is preferably a source providing an electric field, a magnetic field, high energy waves like laser beams or ultrasonic waves, etc. in a special embodiment. The energy source may be a combination of these sources.

In another embodiment the energy source is a source of thermal energy. Such a source can, of course also be combined with a source as mentioned above. For example, a combination of a source of electric energy and a source of thermal energy has the advantage that a compound with a relatively high molecular weight can be delivered in the organism, because the supply of thermal energy will allow a better penetration into tissues due to dilatation effects.

A method of delivering a biologically active agent for enhanced transnasal delivery into the olfactory pathways and/or into the CNS and thereby circumventing the systemic compartment comprises the bringing of the nasal mucosa in the olfactory area in contact with a delivery system. In order to allow for a facilitated insertion of the nasal electrode (s), the nasal mucosa may optionally be treated before or simultaneously with the intranasal insertion of the electrode (s) by using a nasal decongestant, an anaesthetic agent, a vasoconstrictor, or a mixture of thereof. A nasal decongestant, an anaesthetic agent, a vasoconstrictor, or a mixture of thereof may be part of the pharmaceutical composition contained or delivered through the nasal electrode (s) for the delivery of a biologically active agent into the olfactory pathways and/or the CNS. A vasoconstrictive agent includes without limitation epinephrine or phenylephrine. The preferred concentration of epinephrine is from 0.001 to 1 mg/ml, more preferred from 0.01 to 0.5 mg/ml; more preferred from 0.05 to 0.2 mg/ml and most preferred is 0.081 mg/ml. An anaesthetic agent can be any local or topical anaesthetic agent known to those skilled in the art. The most preferred is lidocaine at a preferred concentration of 0.2 to 20%, more preferred 1 to 10% and most preferred is 2%. It is very important to enlarge the nasal passages in order to facilitate the insertion of the intranasal drug delivery device. Also, it is crucial to reduce the amount and viscosity of the nasal mucous in order to enhance the efficiency of drug delivery to the nasal mucosa. The term "nasal decongestant" is used in the present application to describe a substance or a physical parameter (e.g. temperature) that reduces the amount or viscosity of nasal secretions, and/or reduces the thickness of the nasal mucosa thus enlarging the nasal passages. For example, a nasal decongestant can be selected from the following list without limitation: Cocaine (preferably total amount<200 mg), neosynephrine (preferred 0.5%), oxomethazoline, epinephrine, euphedrine, etc. A nasal decongestant with or without a topical anaesthetic and/or a vasoconstrictive agent can be added to the pharmaceutical composition and or being administered prior to the iontophoresis or phonophoresis application in the form of a powdered or liquid nasal spray, nose drops, a gel or ointment, using any available delivery system including a tube, catheter, syringe, by packtail, by pledget, or by intramucosal injection. A nasal decongestant may be precisely targeted to the olfactory region using a means of direct or indirect localization control (e.g. an endoscope or x-ray or any possible other imaging technique known to those skilled in the art).

Alternatively to the use of vasoconstriction in the present disclosed method, the olfactory region may be dilated following insertion of the drug delivery device (i.e. nasal electrode (s)) by use of dilating means such as without limitation iontophoresis, phonophoresis, local heating and/or the use of dilating agents, which may be part of the pharmaceutical composition. For delivery of peptides, polypeptides and proteins the nasal mucosa in the target area may be (pre) treated with substances that inhibit enzymatic breakdown of the therapeutic agent by enzymes in the nasal mucosa, before it enters the olfactory pathways to the central nervous system. Concomitant administration or pretreatment of the nasal mucosa in the target area with enzyme inhibitors could improve the nasal uptake of peptides and proteins as well as of those compounds that are affected by the action of carboxylesterases, Cytochrome P-450 dependent monooxygenases, phosphatases and possible other enzymes that are secreted in the nasal mucous layer. In addition to enzyme inhibitors, penetration enhancers that act directly on the mucosa have an inhibitory effect on enzymatic activity. Examples of such penetration enhancers are bile salts, sodium-dodecylsulphate, medium chain fatty acids and glycyrrhetinic acid derivatives and any other possible compound known to those skilled in the art.

According to a preferred embodiment, the delivery of a biologically active agent is enhanced by means of iontophoresis into the CNS from the olfactory region via the olfactory pathways by using a total current intensity of up to 10 mA between the donor electrode positioned in the nasal cavity and most preferably in the olfactory region of at least one nostril, and a receptor electrode fixed on the back of the head or another place of the head.

According to a variant of this embodiment the delivery of said biologically active agent is enhanced transnasally into the CNS by using either a nasal phonophoresis probe or nasal iontophoresis electrode (s) and said nasal iontophoresis electrode may contain an electrolyte solution and is positioned in the anterior part, thus not in the olfactory region, of the nasal cavity of a mammal. The receptor (iontophoresis) electrode in this embodiment is fixed on the back of the head or another place, while the biologically active agent is applied in the olfactory region in the form of a powdered or liquid nasal spray, nose drops, a gel or ointment, using any available delivery system including a tube, catheter, syringe, by packtail, by pledget, or by intramucosal injection whereafter an electric field and/or ultrasound is applied.

Expediently, the biologically active agent may be administered in the olfactory region separately from the electrode (s) for iontophoresis and/or phonophoresis. The agent can be contained in an electroconductive container or reservoir such as a for example a hydrogel patch that may have mucoadhesive properties in order to hold the agent containing means in the olfactory region for a certain period of time. The electrode for iontophoresis and/or phonophoresis is inserted at appropriate times at or near the location carrying the biologically active agent. Optionally delivery from said container or reservoir is activated by application of an electric field or ultrasound or any other possible energy source known to those skilled in the art.

According to yet another variant of this embodiment the delivery of said active agent is enhanced transnasally into the CNS by using an externally applied phonophoresis probe and/or iontophoresis electrode that may contain an electrolyte solution and this iontophoresis electrode is fixed near or on the bridge of the nose or on the forehead of a mammal. The receptor iontophoresis electrode in this embodiment is fixed on the back of the head or another place, while the biologically active agent is applied in the olfactory region in the form of a powdered or liquid nasal spray, nose drops, a gel or ointment, using any available delivery system including a tube, catheter, syringe, by packtail, by pledget, or by intramucosal injection whereafter an electric field and/or ultrasound is applied.

According to a further variant of the invention, the delivery of said compound is enhanced into some specific region of the brain by using a donor electrode fixed intranasally and a split receptor electrode, whereof one part is fixed externally on the projection of said specific region on the head, and another part is fixed on the back of the head or another place of the head, while the biologically active agent has been applied in the olfactory region.

For the delivery of the active compound in a certain hemisphere or part of a hemisphere it is necessary to fix the donor electrode into one nostril and to fix the split receptor electrode on the mastoideus, or another place of the body.

With reference to the use of the present invention the biologically active agent may be targeted to specific sites within the central nervous system by placing the active agent in a specific site within the olfactory region that corresponds with the target site in the CNS. Drug targeting may be feasible, because the olfactory neurons are represented topographically within the olfactory bulbs and this topographic pattern is suggested to extend more centrally.

It is further observed that the present type of iontophoresis (i.e. according to the invention) can be combined with other methods, which are suited for the delivery of biologically active compounds. Examples of such methods are diathermy, use of magnetic field, use of ultrasonic energy, high energy such as laser etc., or use of compounds providing a dilatation effect. These dilating compounds can either be administered separately via oral or parenteral routes or be combined with the drug delivered via iontophoresis. Diathermy and dilators are preferred when the delivery of biologically active compounds having a high molecular weight must be enhanced through the olfactory region and into the olfactory pathways.

Vehicles or excipients used in conjunction with an apparatus according to the disclosed method include any non-toxic water-soluble compound that is suitable for iontophoretic and/or phonophoretic transport through the olfactory mucosa.

In an another embodiment of the present invention, the biologically active agent is delivered directly to the CNS by the ocular pathway. According to this transocular embodiment the donor electrode is a split electrode and is preferably positioned on the eyelids, whereas the receptor electrode may be placed at the back of the head or the neck.

Variations of this method we called transcorneal and transscleral iontophoretic brain delivery, and can be realized by applying two donor electrodes directly to the cornea and the sclera, respectively. The receptor electrode can be fixed on the back of the head for example in the area of the cervical vertebrae or any other place.

With respect to the electrodes for use in transocular including transcorneal and transscleral delivery to the CNS the same features as those described for transnasal delivery may be applied. The donor electrode (s) being optimally adapted to be positioned on the eyelids or on the cornea or sclera.

An important application of the present invention is for delivery of therapeutic agents that would otherwise not enter the brain due to the presence of the BBB. These agents such as for example peptides can be used to treat for hitherto untreatable disorders. For example, the administration of peptides to a target or affected site in the CNS. Peptides exert important behavioral effects, effects on higher integrative functions of the brain and on the vegetative functions of the CNS. Peptides are thus also involved in the pathogenesis of several brain disorders among the following: Alzheimer's disease, depression, mania, schizophrenia, amnesia, migraine-headache, stroke, insomnia, alcohol abuse, anxiety, obsessive compulsive disorder, cerebral acquired human immuno-deficiency syndrome, chronic pain and many others.

EXAMPLE 1

In an animal study that was approved by the German Animal Care and Use Committee an investigation was made of the effect of transnasal delivery of methylprednisolone on brain levels following 60 minutes of active (current application) and passive (no current application) transport via the olfactory route. The soluble form of methylprednisolone, methylprednisolone hemisuccinate (MW 496.50; $C_{26}H_{33}NaO_8$) was purchased from Sigma Chemicals (Zwijndrecht, The Netherlands). A 20% solution of methylprednisolone hemisuccinate in bidistilled water was prepared and used as donor formulation for cathodal transnasal iontophoresis.

Eight New Zealand White male rabbits, each weighing between 3.0–3.5 kg, were anaesthetised with an intraperitoneal injection of a 25% urethane solution (Riedel-de-Haen; 5 mil/kg). The back and the neck of the animals were shaven to allow for proper skin contact with the receptor electrode. A catheter was placed in the arteria femoralis for blood sample collection. During the experiment the animal was in a supine position, while having its neck and back of its head placed on a receptor electrode pad, which contained a 0.9% sodium chloride solution. Two silverchloride nasal electrodes comprising each 250 μl of the donor formulation in their reservoir were inserted deeply into each nasal passage. Immediately after insertion, a medium frequency interrupted DC current was supplied to the electrodes. A total of 3.0 mA i.e. 1.5 mA per electrode was supplied using an Endomed 581(Enraf Nonius, Delft, The Netherlands) iontophoresis device. This current strength was supplied during 60 minutes to five animals. No current was applied to the electrodes of three control animals.

Blood samples were collected before start of the application (t=0) and at 15, 30, 45 and 60 minutes. After 60 minutes, the nasal electrodes were removed and the animal was sacrificed by means of an intracardial injection of T61, a commercial available mixture of barbiturates that was purchased from Hoechst, Germany. Immediately after euthanasia, the animal's brain was collected for drug analysis. The amount of methylprednisolone in the brain samples was assayed by a high-pressure liquid chromatography (HPLC) method.

Figure 4:
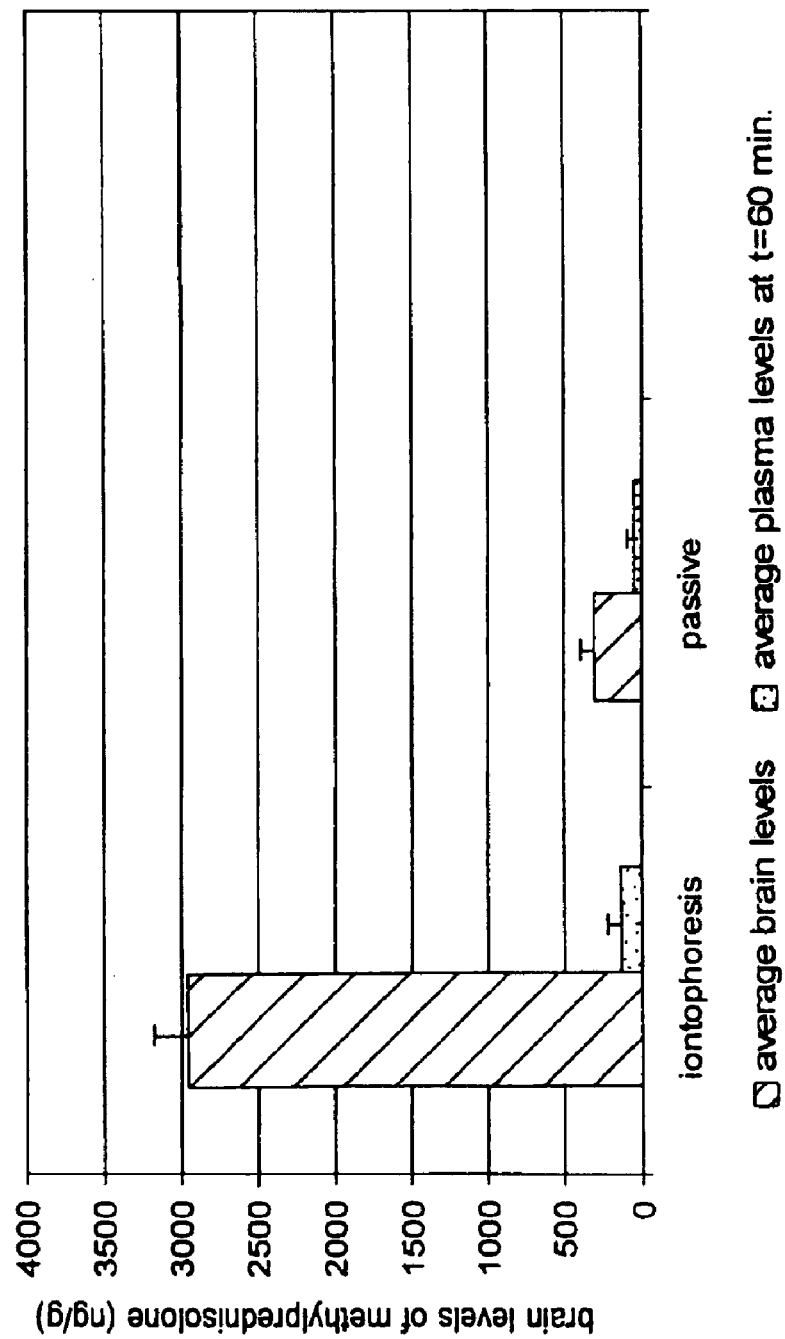
FIG. 4 is a graph displaying the Methylprednisolone brain levels (average±standard deviation) following transnasal iontophoretic delivery in anaesthetised animals.

Results are shown in FIG. 4, the brain levels (average.±standard deviation) of methylprednisolone in ng/g of brain tissue are graphically represented as a function of treatment i.e. transnasal iontophoresis and passive transnasal delivery. Further are shown the plasma levels.

From the results it can be concluded that iontophoresis effectively enhanced the amount of drug entering the central nervous system via the olfactory pathways significantly, while the amount of drug entering the systemic compartment is still comparable to passive transnasal delivery. Therefore, the increase in brain uptake has to be attributed to enhanced transport of the drug directly from the nose into the brain instead of an increase in blood-brain barrier transport of methylprednisolone. The Figure clearly demonstrates the advantage of the method disclosed in the present invention.

EXAMPLE 2

Material and Methods:

The brain levels of Tacrine hydrochloride following transnasal iontophoretic delivery was studied in nine New Zealand white rabbits (weight 3.0–3.5 kg). Tacrine hydrochloride is a drug used in the treatment of Alzheimer's disease but that evokes a large number of adverse (systemic) reactions. The drug was administered by two nasal electrodes that were each deep inserted in the nasal passages. The receptor electrode was positioned at the back of the animal's head. The animal was prior to delivery exsanguinated so that drug transport via the systemic compartment to the brain cannot occur.

A 0.36 M solution of Tacrine hydrochloride monohydrate (9-amino-1,2,3,4-tetrahydroacridine hydrochloride monohydrate) in bidistilled water was used as donor formulation and the two nasal donor electrodes were each filled with 250 μl of the donor formulation. The receptor electrode used in the experiments was saturated with a 0.9% NaCl solution. The iontophoresis apparatus used in these experiment was an Endomed 581 (Enraf Nonius, Delft, The Netherlands) iontophoresis device.

Seven of the nine animals were treated "actively" by means of transnasal iontophoresis. A medium frequency, interrupted direct current with a strength of +3.0 mA was applied to the electrodes immediately after the exsanguination was completed. The remaining two animals functioned as controls of the method and no current was supplied to their electrodes. The experiment lasted 60 minutes. After finishing the experiment, the brain was perfused with 0.9% saline and subsequently collected and dissected in the following parts for drug analysis: left and right temporal lobes, brain stem, the frontal lobe and the brain rest. The frontal lobe was horizontally sectioned in two parts i.e. the basal part and the convexital part.

Results:

Post-mortem investigation of the brain prior to dissection revealed a complete absence of blood in the cranial cavity and brain of all animals. Indicating that the exsanguination as well as the perfusion was successful. Observed Tacrine levels in the selected brain parts of actively treated animals are presented in table 1.

TABLE 1

Tacrine hydrochloride levels (mu.g/g) following transnasal iontophoresis with + 3.0 mA during 60 minutes. Frontal lobe 1 means the basal part and frontal lobe 2 means the convexital part of the frontal lobe.

| Tissue/ | Tacrine hydrochloride levels (mu.g/g) | | | | | | |
|---|---|---|---|---|---|---|---|
| Rabbit numbers: | 1 | 2 | 3 | 4 | 5 | 6 | 7 |
| Frontal lobe 1 | 1.90 | 0.64 | 0.21 | 0.36 | 0.51 | 0.40 | 5.30 |
| Frontal lobe 2 | 0.80 | 1.60 | 0.34 | 0.19 | 0.22 | 0.58 | 2.00 |
| Temporal lobe right | 0.65 | 3.00 | 0.14 | 0.27 | 0.42 | 0.40 | 1.06 |
| Temporal lobe left | 0.53 | 4.50 | 0.19 | 0.33 | 0.53 | 0.71 | 1.41 |
| Brain stem | 1.85 | 0.85 | 0.17 | 0.15 | 0.34 | 0.54 | 0.90 |
| Brain rest | 1.86 | 1.10 | 0.28 | 0.37 | 0.63 | 0.46 | 1.10 |

The results of the control animals are shown in table 2.

TABLE 2

Tacrine hydrochloride brain levels (mu.g/g) following transnasal administration using no iontophoresis (0.0 mA) for 60 minutes. Frontal lobe 1 means the basal part and frontal lobe 2 means the convexital part of the frontal lobe.

| Tissue/ | Tacrine hydrochloride levels (mu.g/g) | |
|---|---|---|
| Rabbit numbers: | 8 | 9 |
| Frontal lobe 1 | <0.10 | <0.10 |
| Frontal lobe 2 | <0.10 | <0.10 |
| Temporal lobe right | <0.10 | <0.10 |
| Temporal lobe left | <0.10 | <0.10 |
| Brain stem | <0.10 | <0.10 |
| Brain rest | <0.10 | <0.10 |

The results in table 2 show that Tacrine hydrochloride could not be recovered in the brain following passive transnasal transport to the brain. Application of iontophoresis resulted in significant brain levels in all selected brain parts. Suggesting that the applied electric field over the two nasal electrodes and receptor electrode is able to advance the charged, lipophilic Tacrine molecules over a distance of at least 5–6 cm. FIG. 5 shows a graphical representation of the obtained results. The observed results are indicative for the migration distance that can be obtained following transnasal iontophoretic delivery via the olfactory pathway as well as following direct iontophoretic delivery via an implantable device.

Modifications and variations of the method and apparatus for iontophoretic enhanced delivery of a biologically active agent into the CNS will be obvious to those skilled in the art from the foregoing detailed description. Such modifications and variations are intended to come within the scope of the appended claims.

It will now be apparent to those skilled in the art that other embodiments, improvements, details, and uses can be made consistent with the letter and spirit of the foregoing disclosure and within the scope of this patent, which is limited only by the following claims, construed in accordance with the patent law, including the doctrine of equivalents.

What is claimed is:

1. A method of delivering a biologically active agent to the central nervous system (CNS) of a mammal utilizing pathways that bypass blood-brain barrier comprising the steps of:

(a) establishing a source of the agent at a zone adjacent a mammal body surface area, the zones being selected from the group consisting of olfactory region, ocular region, brain surface, spinal cord, and intrabrain, (b) establishing a radiant energy gradient from the source to CNS and maintaining the gradiant by energy supply to drive the agent directly from the source to and into the CNS region adjacent the source and within CNS essentially bypassing the mammal's blood-brain barrier, the biological agent being selected of a species and size responsive to the radiant energy driving force and mobile within its selected pathway to and within CNS, but larger than sizes of agents that readily traverse blood-brain barrier.

2. The method of claim 1 wherein the zone is the olfactory system.

3. The method of claim 1 wherein the zone is the ocular (optic nerve) system.

4. The method of claim 1 wherein the zone is the brain.

5. The method of claim 1 wherein the zone is the spinal region.

6. The method of claim 1 wherein the radiant energy driving force is electrophoretic.

7. The method of claim 1 wherein the radiant energy driving force is magnetic.

8. The method of claim 1 wherein the energy driving force is phonophoretic.

9. The method of claim 1 wherein the radiant energy driving force is electromagnetic.

10. The method of claim 1 wherein the radiant energy driving force is high frequency.

11. Apparatus usable in a non-invasive method for enhanced and controlled delivery of a biologically active agent to the central nervous system of a mammal and particularly a human being utilizing the olfactory pathways, the apparatus including:

(i) a first electrode insertable in the olfactory area of said mammal and said first electrode being a donor electrode that is constructed and arranged to be positioned in the olfactory area of a mammal, (ii) a second electrode, the second electrode being a receptor pad electrode constructed and arranged to be positioned on or in proximity to the head of a mammal in one or more locations and constructed and arranged for co-operation with an energy source to establish a radiant energy gradient across at least a portion of the mammal's olfactory area central nervous system, and (iii) means for energizing said first and second electrodes with an energy source providing a potential gradient so that delivery of the biologically active agent is accomplished in a direction from said first electrode means directly into the central nervous system via the olfactory pathways and thereby essentially circumventing the blood-brain barrier of the mammal.

12. The apparatus of claim 11, wherein said energy source is constructed and arranged to provide a type of energy selected from the group consisting of electric energy, magnetic energy, electromagnetic energy, ultrasonic energy, high frequency waves and combinations thereof.

13. The apparatus of claim 1 wherein said first electrode means is of a design and shape, size or material to fit comfortably in a nasal cavity of a mammal and provides an intimate contact with the nasal mucosa in the olfactory area in order to enhance delivery of a biologically active agent via said olfactory area directly into the mammal's central nervous system, thereby essentially circumventing the mammal's blood-brain barrier.

14. Apparatus according to claim 11, wherein said first electrode is a reservoir-type iontophoresis electrode holding a supply of a biologically active agent in a formulation suitable for iontophoretic delivery through the olfactory mucosa and olfactory pathways to the central nervous system.

15. Apparatus in claim 14 wherein said reservoir holds a self-sealing membrane or valve to allow for in-situ refilling.

16. Apparatus according to claim 14, wherein said first electrode comprises an electroconductive part having electroconductive material selected from the group consisting of stainless steel, gold, silver, titanium, copper, zinc, graphite and metal salts.

17. Apparatus according to claim 14, wherein said reservoir of said first electrode means is formed of a polymer matrix containing an electroconductive filler material selected from the group consisting of a metal powder, powdered graphite and carbon fibers.

18. Apparatus according to claim 14, wherein said reservoir is constructed of material that is adapted to absorb, hold and release the biologically active agent.

19. Apparatus according to claim 14, wherein said reservoir comprises a polymeric material consisting of hydrophilic and hydrophobic matrix structure.

20. Apparatus according to claim 14, wherein said reservoir is made of a hydrogel that holds the biologically active agent.

21. A non-invasive method for enhanced and controlled delivery of a biologically active agent to the central nervous system of a mammal and particularly a human being utilizing the olfactory pathways that circumvent the blood-brain barrier, which includes the steps of:

administering a biologically active agent in the olfactory area of a mammal;

inserting a first electrode(s) containing an electrolyte in the anterior part of the nasal cavity;

applying a complementary electrode as a passive iontophoresis electrode on or in proximity to the head of the mammal in one or more locations and to establish a radiant energy gradient across at least a portion of the mammal's central nervous system; and providing a potential gradient between the first and complementary electrode so that delivery of the biologically active agent is facilitated in a direction from said first electrode means directly into the central nervous system via the olfactory pathways and thereby essentially bypassing the blood-brain barrier of the mammal.

22. A method and device as claimed in claim 21 wherein said first electrode is positioned outside the nasal cavity.

23. A non-invasive method for enhanced and controlled delivery of a biologically active agent to the central nervous system of a mammal and particularly a human being utilizing the ocular pathway that circumvent the blood-brain barrier, which includes the steps of:

applying a first active iontophoresis electrode on an eyelid of said mammal;

applying a second passive iontophoresis electrode on or in proximity to the head of the mammal in one or more locations and constructed and arranged for co-operation with an energy source to establish a radiant energy gradient across at least a portion of the mammal's central nervous system; and providing a potential gradient so that delivery of the biologically active agent is accomplished in a direction from said first electrode means directly into the central nervous system via the ocular pathway and thereby essentially bypassing the blood-brain barrier of a mammal.

24. A method as claimed in claim 23, wherein an energy source selected from the group consisting of electric energy, magnetic energy, electromagnetic energy, high frequency wave sources and combinations thereof is used to provide a potential gradient.

25. Apparatus for enhanced and controlled delivery of a biologically active agent to the central nervous system of a mammal and particularly a human being utilizing the ocular pathway which includes:

a first active iontophoresis electrode that is constructed and arranged to be positioned on an eyelid of said mammal;

a second passive iontophoresis electrode that is constructed and arranged to be poisitioned on or in proximity to the head of the mammal in one or more locations and constructed and arranged for co-operation with an energy source to establish a radiant energy gradient across at least a portion of the mammal's central nervous system; and means for providing a potential gradient so that delivery of the biologically active agent is accomplished in a direction from said first electrode means directly into the central nervous system via the ocular pathway and thereby essentially bypassing the blood-brain barrier of the mammal.

26. An invasive method for enhanced and controlled delivery of a biologically active agent to the central nervous system of a mammal that circumvents the blood-brain barrier, which includes the steps of:

positioning a first electrode or donor iontophoresis electrode that is constructed and arranged to be positioned on the brain surface or intrabrain of a mammal and applying a receptor iontophoresis electrode within the mammal's head or on the exterior surface, providing an energy potential gradient so that delivery of the biologically active agent is accomplished in a direction from said first electrode means directly into the central nervous system thereby essentially bypassing the blood-brain barrier.

27. Apparatus for enhanced and controlled delivery of a biologically active agent to the central nervous system of a mammal that bypasses the blood-brain barrier, which comprises:

a first electrode or donor iontophoresis electrode that is constructed and arranged to be positioned on the brain surface or internally of the brain of the mammal and a further receptor iontophoresis electrode in or outside the mammal's head, means for providing an energy potential gradient so that delivery of the biologically active agent is accomplished in a direction from said first electrode means directly into the central nervous system thereby essentially bypassing the blood-brain barrier.

28. A method and device for enhanced and controlled delivery of a biologically active agent locally of the spinal cord or another portion of the central nervous system of a mammal that circumvents the blood-brain barrier, which includes the steps of:

positioning a first donor iontophoresis electrode that is at or in close vicinity of the spinal cord of the mammal and applying a second receptor iontophoresis electrode in an internal complementary body location so that the two electrodes span the spinal cord;

providing a potential gradient between the electrodes so that delivery of the biologically active agent is accomplished in a direction from said first electrode means directly into the adjacent spinal tissue on another portion of the central nervous system thereby essentially bypassing the blood-brain barrier of the mammal; and delivering said active substance into the spinal cord of said mammal.

29. Apparatus for enhanced and controlled delivery of a biologically active agent to a local spinal cord region or another portion of the central nervous system of a mammal that circumvents the blood-brain barrier, comprising:

a first electrode or donor iontophoresis electrode that is constructed and arranged to be positioned in close vicinity of the spinal cord of the mammal and a second receptor iontophoresis electrode that is constructed and arranged to be positioned in an internal complementary body location;

means for providing a potential gradient so that delivery of the biologically active agent is accomplished in a direction from said first electrode means directly into the adjacent spinal tissue or another portion of the central nervous system thereby essentially bypassing the blood-brain barrier of the mammal;

30. A phonophoresis method of delivering a biologically active agent to the central nervous system (CNS) of a mammal utilizing pathways that bypass the blood-brain barrier with minimal surgical intervention comprising the steps of:

(a) establishing a source of the agent at a zone adjacent a mammal body surface area, the zones being selected from the group consisting of olfactory region, ocular region, brain surface, spinal cord, (b) establishing a radiant energy gradient from the source to CNS and maintaining the gradiant phenopheretic by energy supply to drive the agent directly from the source to and into the adjacent CNS region and thereby essentially bypassing the mammal's blood-brain barrier, the biological agent being selected of a species and size responsive to the radiant energy gradient and mobile within its selected pathway to and within CNS, but Larger than sizes of agents that readily traverse blood-brain barrier.

31. Apparatus for enhanced and controlled delivery of a biologically active agent to the central nervous system of a mammal and particularly a human being utilizing the olfactory pathways that circumvent the blood-brain barrier, the apparatus including:

a first electrode insertable in the olfactory area of said mammal, said first electrode being a donor electrode that is constructed and arranged to be positioned in the olfactory area of a mammal, a second electrode, constructed and arranged to be positioned on or in proximity to the head of a mammal in one or more locations and constructed and arranged for co-operation with an energy source to establish a radiant energy gradient across at least a portion of the mammal's olfactory area central nervous system; and means for energizing said first and second electrodes with an energy source providing a potential gradient so that delivery of the biologically active agent is accomplished in a direction from said first electrode means directly into the central nervous system via the olfactory pathways, essentially circumventing the blood-brain barrier of the mammal.

* * * * *